United States Patent [19]

Vlahov et al.

[11] 4,239,605
[45] Dec. 16, 1980

[54] METHOD FOR THE ELECTROLYTIC PREPARATION OF NARWEDINE-TYPE DIENONES

[75] Inventors: Radoslav Y. Vlahov; Dikran A. Krikoryan; Maria S. Zagorova; Maya H. Hinova; Stoyan P. Parushev, all of Sofia, Bulgaria

[73] Assignee: Edinen Centar Po Chimia, Sofia, Bulgaria

[21] Appl. No.: 94,351

[22] Filed: Nov. 14, 1979

[30] Foreign Application Priority Data

Nov. 21, 1978 [BG] Bulgaria ................................. 42315
Nov. 21, 1978 [BG] Bulgaria ................................. 41458

[51] Int. Cl.³ ................................................ C25B 3/00
[52] U.S. Cl. .................................................. 204/59 R
[58] Field of Search ..................................... 204/59 R

[56] References Cited

U.S. PATENT DOCUMENTS 3,446,718   5/1969   Inoue ..................................... 204/59

Primary Examiner—R. L. Andrews

[57] ABSTRACT

A method for the preparation of narwedine-type dienones involves electrochemical oxidation of diphenolic derivatives in an organic solvent medium containing a conductive salt at a potential ranging from 1.1 to 1.7 volts. The dienones so obtained are of high purity and are produced in good yields.

2 Claims, No Drawings

METHOD FOR THE ELECTROLYTIC PREPARATION OF NARWEDINE-TYPE DIENONES

This invention relates to a method for the preparation of narwedine-type dienones. More particularly, the present invention relates to a method for the preparation of narwedine-type dienones by electrochemical oxidation.

The narwedine-type dienones are known compounds which are typically employed as the starting material in the synthesis of Amaryllidaceae alkaloids. This end is normally attained by the oxidation of diphenolic derivatives. Unfortunately, such prior art procedures result in the formation of a large number of by-products which are difficult to separate and of little or no known use.

In accordance with the present invention, these prior art limitations are effectively obviated by a novel technique which results in the production of a high purity narwedine-type dienone in high yields. The resultant dienone may subsequently be transformed chemically into Amaryllidaceae alkaloids. Briefly, the invention involves forming the desired dienones by the electrochemical oxidation of diphenolic derivatives of the general formula

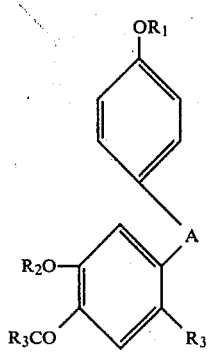

wherein A is selected from the group consisting of

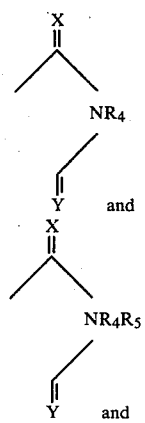

X and Y are selected from the group consisting of $H_2$ and O, $R_1$, $R_2$ and $R_5$ being an alkylic group selected from the group consisting of $CH_2C_6H_5$ and $CH_2C_6H_4OCH_3$, $R_3$ representing a halogen atom and $R_4$ representing $HClO_4$ and similar salts of organic and inorganic acids.

The dienones obtained in accordance with the oxidation are of the general formula

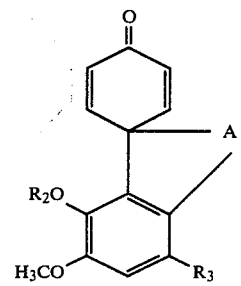

wherein A, $R_2$ and $R_3$ are as represented above.

The electrochemical oxidation hereindescribed is effected in an electrolytic cell having separate anode and cathode compartments, and an organic solvent medium containing a conductive salt at a working potential ranging from 1.1 to 1.7 volts. The solvent medium found to be particularly useful for this purpose is methyl cyanate. Typical of the conductive salts selected for use are $LiClO_4$, $KClO_4$, $NaClO_4$, $(C_4H_9)_4NBF_4$ and $(C_2H_5)_4NBF_4$.

Electrodes employed herein as the working electrode may be of platinum, graphite and the like, the potential being measured by means of a reference electrode. The medium in which oxidation is effected may be maintained in either an acidic, alkaline or neutral condition by the use of additives such as $Na_2CO_3$, $K_2CO_3$, $NaHCO_3$, $HBF_4$, $CH_3COOH$ and the like.

As indicated, the prime advantage of the described method resides in the high level of purity of the final product. Unreacted starting material found with the final product is readily separated and recycled for further use in the process. Yield is found to be of the order of 40%, such being higher than that attained by means of the known methods of chemical oxidation.

Examples of the invention are set forth below. It will be appreciated by those skilled in the art that these examples are for purposes of exposition only and are not intended to be limiting.

EXAMPLE 1

This example describes the preparation of 8-bromo-9-oxo-O,O' dimethylhydroxyapogallantamine by electrolytic oxidation of N-methyl-(4-methoxyphenethyl)-2-bromo-4,5-dimethoxybenzamide in accordance with the following reaction:

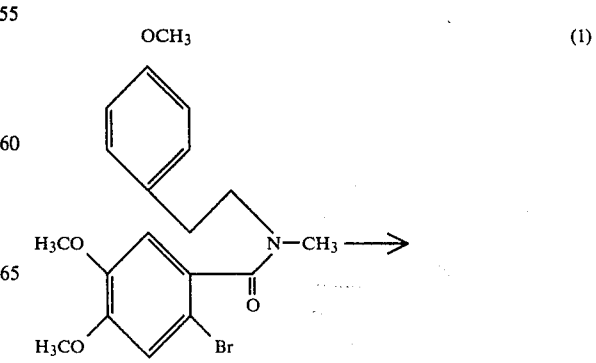

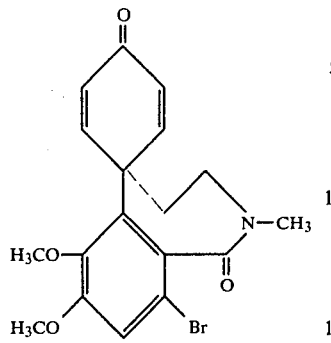

To the anode compartment of an electrolytic cell was added 0.001 mole of N-methyl-(4-methoxyphenylethyl)-2-bromo-4,5-dimethoxybenzamide in a methyl cyanate solvent (benzamide to solvent ratio of 1:100) containing 2.4% $(C_4H_9)_4NBF_4$ (conductive salt) and 2% $HBF_4$ (acid) or $KClO_4 + K_2CO_3$. The cathode compartment and the electrolytic bridge of the reference electrode contained the anodic solvent and the same percentage of conductive salt. The working electrode was platinum and the reference electrode $Ag/Ag^+$ in methyl cyanate. The oxidation was carried out at 1.3 volts at a temperature below 0° C. until the equivalent electric charge has flown, approximately 3–5 hours. Following conclusion of the process, the anode compartment was evaporated to dryness and the residue dissolved in chloroform and washed in bicarbonate solution and water. After drying the solution, the solvent was evaporated and the residue purified by chromatography or recrystallization. The yield or narwedine dienones was 40%.

EXAMPLE 2

This example describes the preparation of narwedine type dienones by electrolytic oxidation of N-methyl (4'-benzyloxyphenetyl)-2-bromo-4-methoxy-5-benzyloxybenzamid in accordance with the following reaction:

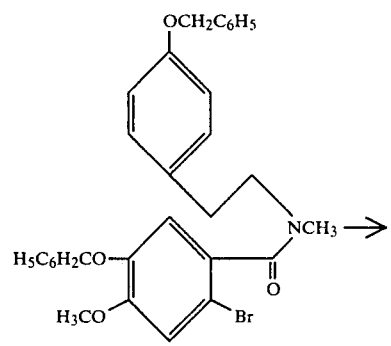

(2)

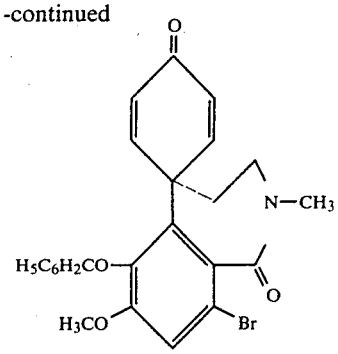

The procedure followed was that employed in Example 1 and the yield obtained of the desired apogallantamine was comparatively good with respect thereto.

What is claimed is:

1. Method for the preparation of narwedine-type dienones and derivatives thereof of the formula

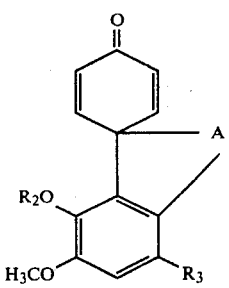

wherein A is selected from the group consisting of

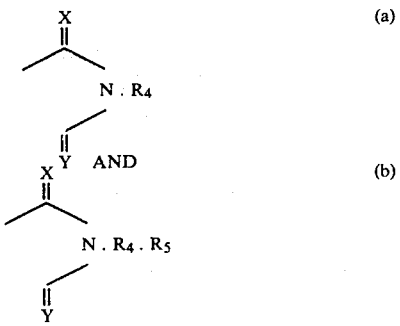

X and Y being selected from the group consisting of $H_2$ and O, $R_2$ and $R_4$ being low order alkylic groups selected from the group consisting of $CH_2C_6H_5$ and $CH_2C_6H_4OCH_3$, $R_3$ being a halogen atom and $R_5$ being $HClO_4$ and similar salts of an organic or morganic acid which comprises electrochemically oxidizing a diphenolic compound of the formula

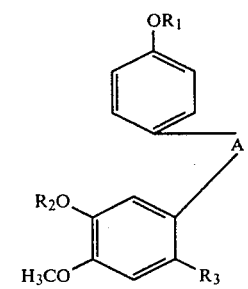

wherein $R_1$, is selected from the group consisting of low order alkylic groups of the formula $CH_2C_6H_5$ and $CH_2C_6H_4OCH_3$ and $R_2$ and $R_3$ are as defined above, said oxidizing being effected at an anode potential ranging from 1,1 to 1.7 volts in the presence of a solvent and a conductive salt.

2. Method in accordance with claim 1, wherein said conductive salt is selected from the group consisting of $KClO_4$, $LiClO_4$, $(C_4H_9)_4 NBF_4$ and $(C_2H_5)_4 NBF_4$.

* * * * *